| United States Patent [19] | [11] 4,138,498 |
|---|---|
| Das | [45] Feb. 6, 1979 |

[54] RUMINANT FEED ADDITIVE

[75] Inventor: Naba K. Das, Ellicott City, Md.

[73] Assignee: W. R. Grace & Co., New York, N.Y.

[21] Appl. No.: 748,210

[22] Filed: Dec. 7, 1976

[51] Int. Cl.$^2$ ............................................. A23K 1/18
[52] U.S. Cl. ............................................ 426/2; 426/61; 426/623; 426/630; 426/636; 426/807; 424/93
[58] Field of Search ............... 426/2, 636, 61, 623, 426/807, 630; 424/93, 104; 195/96

[56] References Cited

PUBLICATIONS

Huber et al., "Lactic Acid Utilizing Bacteria in Ruminal Fluid of a Steer Adapted from Hay Feeding to a High Grain Ration", Am. J. Vet. Res., vol. 37, No. 5, pp. 611-613, May 1976.

Bergey, "Manual of Determinative Bacteriology" Williams & Wilkens Publishing Co., (1974), pp. 425-426.

*Primary Examiner*—R. B. Penland
*Attorney, Agent, or Firm*—Philip M. Pippenger; William W. McDowell, Jr.

[57] ABSTRACT

Disclosed herein is an improved feed additive for administration to ruminants to prevent or minimize lactic acidosis when the ruminant is switched from a diet of roughage to starch (high energy). The additive comprises a bacterial culture of *Megasphaera elsdenii* admixed with an ingestible animal feed additive. The additive utilizes the unexpected ability of *M. elsdenii* to ferment lactic acid in preference to simple sugars, thereby minimizing accumulation of lactic acid. The preferred embodiment is the combination of *M. elsdenii* with substances (including bacterial cultures) producing ruminal propionic acid, thereby providing a high propionic level while avoiding lactic acid accumulation.

14 Claims, No Drawings

RUMINANT FEED ADDITIVE

Changing the diet of a ruminant abruptly from hay or other nutrients consumed on pasture to the high energy feed or feed concentrate given when the animals are brought from pasture into feed lots, often leads to acute indigestion which results in varying degrees of prolonged inappetence and sometimes death. Among the reactions that a ruminant can be expected to exhibit upon ingestion of excessive amounts of grain in the feed lot are a rapid accumulation of lactic acid in the rumen, a fall in ruminal pH, an abrupt rise of lactate circulation in the peripheral blood, and a decrease in blood volume and pH along with hemoconcentration. Excessive grain or glucose ingestion can have fatal results in ruminants causing a fall in the pH in the rumen to between 4 and 5 in a few hours, destruction of protozoa, cellulolytic bacteria and lactate utilizing organisms, and a relatively large increase of Gram-positive organisms particularly "*Streptococcus bovis*", a lactic acid producer. A low pH in the rumen produces stasis of that organ which persists for hours even after the pH is restored to a normal level. Most of these adverse reactions can be attributed, at least in part, to abnormally large amounts of lactic acid in the rumen. A ruminant exhibiting some or all of the above symptoms is said to be suffering from "lactic acidosis".

Recently, several treatments for lactic acidosis have been proposed. British Pat. No. 1,251,483 describes a newly discovered organism reportedly having the ability to ferment lactic acid. It is suggested that the organism be administered to ruminants to avoid or alleviate the symptoms of lactic acidosis. U.S. Pat. No. 3,857,971 is based on the discovery that rumen bacteria must be completely conditioned to a high energy ration before being administered to the ruminant. Therefore, samples of rumen microflora and microfauna are cultured in vitro on a high energy starch (as opposed to roughage) ration before administration.

Another publication of interest is Huber et al (Am. J. Vet. Res., Vol. 37, No. 5, pages 611-613) describing analysis of rumen fluid during adaptation of cattle to a high energy ration. The object of the study was to discover bacteria having the ability to utilize lactic acid and therefore proliferate during the adaptation process. Lactic acid utilizing bacteria found to be present include *Megasphaera elsdenii, Peptococcus asaccharolyticus* and *Selenomonas ruminantium*. *M. elsdenii* appeared to flourish during the initial stages of adaptation but the population declined significantly in the adjusted rumen fluid. Both *P. asaccharolyticus* and *S. ruminantium* exhibited higher counts in cultures obtained from the adjusted rumen fluid.

DESCRIPTION OF THE INVENTION

It has now been found that administration to a ruminant of a lactic-acid-utilizing strain of bacteria can alleviate or prevent the gastrointestinal upset and acidosis normally encountered when the animal is transferred to a high-energy diet from a normal pasture diet.

The present invention provides a composition for administration to ruminants to alleviate the symptoms of acidosis which comprises a bacterial culture having lactic acid utilization ability admixed with a carrier. When utilized in the form of a drench, the composition comprises the bacterial culture with an aqueous nutrient media serving as the carrier. When utilized in the form of a pre-mix or feed supplement, the composition comprises the bacterial culture admixed with an orally ingestible animal feed additive serving as carrier.

The invention also comprises a method of facilitating the adaptation of ruminants to a high energy diet by administering to the animal an effective amount of a bacterial culture, said bacterial culture having lactic acid utilization ability.

Specifically the composition of the invention is a bacterial culture of *Megasphaera elsdenii* admixed with a carrier. According to the invention adaptation of ruminants to a high energy ration is facilitated by administering an effective amount of *M. elsdenii* to the ruminant, preferably at the beginning of the adaptation period.

The advantages of the invention are numerous. It has been discovered from in vitro studies that *M. elsdenii* has an unexpectedly large capacity to ferment lactic acid to form volatile fatty acids (VFA), especially butyric. Therefore, even though other bacteria are present which produce lactic acid, the culture of *M. elsdenii* is able to ferment substantially all the output from these bacteria so that there is not an accumulation of lactic acid. Specifically, when grown in vitro with *Streptococcus bovis,* a known heavy producer of lactic acid, *M. elsdenii* was able to remain viable and utilize the lactic acid produced to the extent that the acid could not be detected by gas chromatography.

The unexpectedly high capacity of *M. elsdenii* to utilize lactic acid is believed to result from an unexpected and heretofore unknown preference of this bacterium for lactic acid as a fermentation substrate. In in vitro studies where a number of other starch fermentation products (e.g. peptone, yeast extract and glucose) could be presumed to be present and available, the *M. elsdenii* organism continued to utilize lactic acid produced by other bacteria (e.g. *S. bovis*) present in the fermentation medium.

The unexpected selectivity of *M. elsdenii* for lactic acid also confers another significant advantage in that cultures of *M. elsdenii* can be employed in combination with substances known to increase production of propionic acid in the rumen. It is known that ruminal fermentation produces three principal VFA's, which are acetic, propionic, and butyric acids. Production of acetic and butyric is accompanied by considerable losses in energy. However, propionic acid is produced from simple sugars without the loss of any carbon dioxide or hydrogen. The net result is that there is little or no loss in utilizable energy when simple sugars are converted into propionic acid.

In vitro studies have shown that cultures of *M. elsdenii* in combination with substances producing propionic acid function to increase propionic acid levels, while simultaneously avoiding an accumulation of lactic acid. For example, when *M. elsdenii* was combined with *Selenomonas ruminantium,* propionic acid levels were increased, the ratio of acetic to propionic acids declined, and accumulation of lactic acid was avoided. It is believed that *S. ruminantium* produces lactic acid in addition to propionic acid. it is the unexpected selectivity of *M. elsdenii* for lactic acid which makes the combination beneficial. In addition to *S. ruminantium,* it is believed that *M. elsdenii* can also be employed in combination with other propionic acid-producing organisms such as *veillonella alcalescens, Succinimonas amylolytica* and *Anaerovibrio lipolytica.* In vitro studies have also demonstrated that *M. elsdenii* can be employed in combination with monensin, an antibiotic produced by

*Streptomyces cinnamonensis* and sold by Ely Lilly Co. under the trademark Rumensin. Monensin is known to increase ruminal production of propionic acid.

Cultures of *M. elsdenii* and *Selenomonas ruminantium* have been deposited with ARS Culture Collection Investigations, Northern Utilization Research and Development Division, U.S. Department of Agriculture, Peoria, Illinois 61604, and added to its permanent culture collection as NRRL B-11052 and NRRL B-11051. These bacteria are also readily available and can be easily isolated from rumen fluid according to conventional techniques.

Preparation of Cultures

The deposited cultures were prepared using standard anaerobic techniques as described in the Anaerobe Laboratory Manual by Holdeman and Moore (2nd ed.) published in 1972 under the auspices of the Virginia Polytechnic Institute and State University, Anaerobe Laboratory, Blacksburg, Va.

The cultures were isolated from a material known as ARM (adapted rumen microorganisms). The ARM material is a culture of ruman microflora or organisms grown on a specific high-starch medium. Preparation of the ARM material is described in U.S. Pat. No. 3,857,971 incorporated herein by reference to the extent it describes the ARM preparation.

Outlining the method of isolation from the ARM material and preparation of cultures generally, 1 ml samples of ARM cultures were processed through serial 10-fold dilutions in tubes of anaerobic dilution fluid (dilution blanks) of composition as set forth in Table I.

Table I

| | |
|---|---|
| gelatin | 0.2 g |
| distilled water | 50.0 ml |
| salts solution* | 50.0 ml |
| resazurin solution** | 0.4 ml |
| $CaCl_2$ (anhydrous) | 0.2 g |
| $MgSO_4 \cdot 7H_2O$ | 0.2 g |
| $KH_2PO_4$ | 1.0 g |
| $K_2HPO_4$ | 1.0 g |
| $NaHCO_3$ | 10.0 g |
| NaCl | 2.0 g |

*salts solution - The following materials were dissolved in 1 liter of distilled water.
**resazurin solution - Dissolve 25 mg of resazurin in 100 ml distilled water One ml. of serial dilutions of $10^6$, $10^7$, and $10^8$ of the ARM/dilution blank media was used to inoculate a rumen fluid — glucose — cellobiose — agar (RGCA) solution having the composition set forth in Table II.

Table II

| | |
|---|---|
| Glucose | 0.0248 g |
| Cellubiose | 0.0248 g |
| Soluble Starch | 0.05 g |
| $(NH_4)_2SO_4$ | 0.1 g |
| Resazurin Solution | 0.4 ml |
| Distilled Water | 20.0 ml |
| Salts Solution* | 50.0 ml |
| Rumen Fluid | 30.0 ml |
| Cysteine $HCl-H_2O$ | 0.05 g |
| Agar | 2.00 g |

*as in preceding Table I.

For inoculation, the RGCA medium was placed in a roll tube (25 × 142 mm) and inoculation was carried out under oxygen-free $CO_2$. After inoculation the tubes were inverted gently to mix the contents, and the agar was solidified while rotating and cooling the tubes. Subsequently, the tubes were incubated for four days at 37° C.

Following incubation, the roll tubes were marked with spiral lines, and the colonies were counted using a dissecting microscope. Fifty well-isolated colonies were picked in succession from top to bottom of each tube. Each colony was transferred into 3 ml. of modified peptone yeast extract glucose (PYG) broth with added vitamin K/hemin solution. The modified broth composition is set forth in Table III.

Table III

| | |
|---|---|
| Peptone | 1.0 g |
| Yeast Extract | 1.0 g |
| Resazurin Solution | 0.4 ml |
| Salts Solution* | 4.0 ml |
| Distilled Water | 100.0 ml |
| Cysteine $HCl.H_2O$ | 0.05 g |
| Glucose | 1.0 |
| Vitamin K/hemin Solution** | 1.0 ml |

*as in preceding Table I
**Vitamin K/hemin solution - Menadione stock solution. Add 100 mg Menadione to 20 ml 95% ethyl alcohol. Filter Sterilize.

Hemin stock solution: Dissolve 50 mg hemin in 1 ml 1N NaOH and make to 100 ml with distilled water. Autoclave at 121° C. for 15 min.

Add 1 ml sterile Menadione stock solution to 100 ml hemin stock solution. Use 1 ml of this VK-H solution in 100 ml medium. Menadione is the Nutritional Biochemicals Corporation brand of vitamin K.

The cultures in modified PYG broth were incubated at 37° C. for from 24 to 48 hours. The organisms were identified by gram-staining, analysis of volatile fatty acids (by gas chromatograph), cellular morphology and fermentation studies. The ARM material yielded cultures (maintained in modified PYG broth) of a large number of rumen bacteria including *Megasphaera elsdenii*, *Streptococcus bovis*, *Lactobacillus acidophilus*, *Bifidobacterium adolescentis*, *Bacteriodes ruminicola*, *Butyrivibrio fibrisolvens*, and *Selenomonas ruminantium*.

EXAMPLE I

Lactic Acid Utilization of *M. elsdenii* In Modified PYG Broth

Pure cultures of various rumen organisms isolated from ARM material were grown anaerobically at 37° C. for 23 hours. Adequate mixing was insured by agitating the culture containers at 100 RPM. At the end of the incubation period, the pH and fermentation end products were determined as set forth in Table IV. The level of inoculum was 1% by volume of the PYG broth. Where two organisms were grown together simultaneously, the level was 0.5% of a seed culture of each organism. In Run 6 the level was 0.33%.

TABLE IV

In vitro Lactic Acid Production from Glucose Fermentation and Its Subsequent Utilization by a Lactate Utilizer[a]

| | | | Fermentation End Products ($\mu$ mole/ml) | | |
|---|---|---|---|---|---|
| Run | Organism | pH | Acetic | Propionic | Butyric | Lactic |
| 1 | B. adolescentis | 4.2 | 88.0 | 0.0 | 0.0 | 40.0 |
| 2 | Selenomonas ruminantium | 4.25 | 25.5 | 20.0 | 0.0 | 57.0 |
| 3 | M. elsdenii | 5.9 | 0.0 | 0.0 | 18.5 | 0.0 |
| 4 | B. adolescentis + M. elsdenii | 5.1 | 24.5 | 0.0 | 44.0 | 0.0 |
| 5 | S. ruminantium + M. elsdenii | 5.15 | 17.8 | 24.5 | 22.5 | 0.0 |
| 6 | B. adolescentis + S. ruminantium + M. elsdenii | 4.8 | 46.0 | 21.8 | 20.5 | 0.0 |

[a]Organisms were grown at 37° C for 23 hrs. in a G-25 incubator shaker with 100 RPM following which pH and fermentation end products were determined.

From Table IV it can be seen that *B. adolescentis* and *S. ruminantium* yield a relatively large amount of lactic acid. *M. elsdenii*, however, yields primarily butyric with no lactic, acetic or propionic acids being detected. Unexpectedly, when *M. elsdenii* is grown simultaneously with organisms which produce lactic acid, the utilization capacity of *M. elsdenii* for lactic acid is still sufficiently great that no lactic acid is detectable. In Run 6, no lactic acid is detectable even though both *B. adolescentis* and *S. ruminantium* are present, and the amount of *M. elsdenii* employed initially was reduced to 0.33%. Table IV suggests that *M. elsdenii* utilized lactic acid produced by the other organisms and has a capacity sufficiently high so that there is no accumulation of lactic acid to be detected.

EXAMPLE 2

In Vitro Lactic Acid Utilization in Presence of Rumen Fluid and High Energy Ration This example illustrates the ability of *M. elsdenii* cultures to remain viable in the presence of normal rumen microorganisms and the lactate medium associated with a high energy starch feed.

The rumen contents of a roughage-fed, disease-free steer were withdrawn by means of a stomach pump. The contents were filtered through cheese cloth and transferred in 10 ml. batches into flasks. To each flask was added 1 gram of a starch-based feed having the composition set forth in Table Va.

Table Va

| Ingredient | 87% Concentrate Pounds |
|---|---|
| Ground corn cobs | 38.75 |
| Dehydrated alfalfa meal | 26.50 |
| Ground corn | 342.00 |
| Dried beet pulp | 53.00 |
| Cane molasses on soybean meal feed | 13.25 |
| Protein supplement* | 26.50 |

| Ingredient | Amount |
|---|---|
| Soybean meal | 30.0 lb. |
| Dehydrated alfalfa meal | 22.5 lb. |
| Meat meal | 15.0 lb. |
| Urea | 9.5 lb. |
| Dicalcium phosphate | 5.0 lb. |
| Ground limestone | 3.25 lb. |
| NaCl and trace minerals | 12.5 lb. |
| Vitamin A, D, and E premix | 2.9 grams |

*the protein supplement was prepared by mixing the following ingredients:

Each flask received 1% by weight of a PYG bacterial inoculum prepared as in Example 1. Where more than one inoculum was added, each was employed in equal parts by weight with the total not equalling 1% by weight of the combined rumen fluid/feed/inoculum mixture. As in Example 1, the flasks were incubated at 37° C. for 24 hours with gentle mixing action. After 24 hours, the contents of each flask were analyzed for pH, volatile fatty acids and lactic acid (by gas chromatograph) to yield the results set forth in Table V. The control did not receive inoculum and the fermentation products are the result of organisms present in the rumen fluid.

TABLE V

| Run | Organism[b] | pH | Ac.[a] | Pr[a] | Bu[a] | V[a] | μ moles/ml Lactic | Ratio Ac/P |
|---|---|---|---|---|---|---|---|---|
| 1 | A | 5.0 | 74.3 | 17.4 | 8.3 | 0.0 | 27.0 | 4.3 |
| 2 | B | 5.1 | 67.5 | 23.5 | 9.0 | 0.0 | 31.0 | 2.9 |
| 3 | C | 5.15 | 69.1 | 22.1 | 8.8 | 0.0 | 21.0 | 3.1 |
| 4 | D | 5.25 | 58.7 | 20.0 | 19.0 | 2.3 | 0.0 | 2.9 |
| 5 | E | 5.15 | 76.6 | 23.4 | 0.0 | 0.0 | 31.1 | 3.3 |
| 6 | G | 5.15 | 69.8 | 21.2 | 9.0 | 0.0 | 25.7 | 3.3 |
| 7 | D+G | 5.25 | 59.4 | 19.8 | 18.0 | 2.8 | 0.0 | 3.0 |
| 8 | A+G | 5.0 | 73.7 | 18.3 | 8.0 | 0.0 | 22.4 | 4.0 |
| 9 | A+D+G | 5.05 | 66.9 | 16.7 | 14.6 | 1.8 | 0.0 | 4.0 |
| 10 | A+B | 5.0 | 70.9 | 21.4 | 7.7 | 0.0 | 18.6 | 3.3 |
| 11 | A+C | 5.0 | 72.0 | 20.5 | 7.5 | 0.0 | 16.1 | 3.5 |
| 12 | A+D | 5.05 | 66.6 | 17.5 | 13.9 | 2.0 | 0.0 | 3.8 |
| 13 | A+E | 5.10 | 72.9 | 19.1 | 8.0 | 0.0 | 18.4 | 3.8 |
| 14 | B+C | 5.2 | 66.9 | 24.7 | 8.4 | 0.0 | 20.2 | 2.7 |
| 15 | B+D | 5.2 | 61.3 | 22.6 | 13.7 | 2.4 | 0.0 | 2.7 |
| 16 | B+E | 5.15 | 66.7 | 24.5 | 8.8 | 0.0 | 16.8 | 2.7 |
| 17 | C+D | 5.30 | 60.6 | 20.8 | 18.6 | 0.0 | 0.0 | 2.9 |
| 18 | C+E | 5.15 | 67.7 | 23.1 | 9.2 | 0.0 | 18.2 | 2.9 |
| 19 | D+E | 5.22 | 60.1 | 20.8 | 16.4 | 2.7 | 0.0 | 2.9 |
| 20 | A+B+C | 5.0 | 69.1 | 23.1 | 7.8 | 0.0 | 18.4 | 3.0 |
| 21 | A+B+D | 5.13 | 62.8 | 20.4 | 14.2 | 2.6 | 0.0 | 3.1 |
| 22 | A+B+E | 5.0 | 70.8 | 21.7 | 7.5 | 0.0 | 20.4 | 3.3 |
| 23 | A+C+D | 5.0 | 67.6 | 17.5 | 13.1 | 1.8 | 0.0 | 3.9 |
| 24 | A+C+E | 5.0 | 72.4 | 19.8 | 7.8 | 0.0 | 22.8 | 3.7 |
| 25 | A+D+E | 5.04 | 66.2 | 18.0 | 13.6 | 2.2 | 0.0 | 3.7 |
| 26 | B+C+D | 5.2 | 63.1 | 23.0 | 12.1 | 1.8 | 0.0 | 2.7 |
| 27[h] | B+C+E | 5.1 | 66.0 | 25.0 | 9.0 | 0.0 | 0.0 | 2.6 |
| 28 | B+D+E | 5.2 | 63.2 | 22.1 | 12.5 | 2.2 | 0.0 | 2.9 |
| 29 | C+D+E | 5.2 | 64.3 | 21.7 | 14.0 | 0.0 | 0.0 | 3.0 |
| 30 | A+B+C+D | 5.1 | 65.2 | 21.7 | 13.1 | 0.0 | 0.0 | 3.0 |
| 31 | A+B+C+E | 5.02 | 69.4 | 23.3 | 7.3 | 0.0 | 17.8 | 3.0 |
| 32 | A+B+D+E | 5.05 | 67.8 | 19.8 | 12.4 | 0.0 | 0.0 | 3.4 |
| 33 | A+C+D+E | 5.06 | 67.4 | 19.0 | 13.6 | 0.0 | 0.0 | 3.5 |
| 34 | B+C+D+E | 5.15 | 63.2 | 24.3 | 12.5 | 0.0 | 0.0 | 2.6 |
| 35 | A+B+C+D+E | 5.15 | 65.8 | 21.8 | 12.4 | 0.0 | 0.0 | 3.0 |
| 36 | Control | 5.10 | 69.0 | 21.4 | 9.6 | 0.0 | 26.1 | 3.2 |

[a] Ac - acetic; Pr- propionic; Bu - butyric; V - valeric
[b] A - *Bifidobacterium adolescentis*
B - *S. ruminantium* (large curved rods) - Culture WRC F5R-6
C - *S. ruminantium* (smaller, thinner rods)
D - *M. elsdenii* - Culture WRC 80-31
E - *B. ruminicola*
G - *Streptococcus bovis*
[h] This sample is believed to be in error since organisms B, C and E all produced lactic acid in monocultures.

From Table V it will be noted that *M. elsdenii* (organism D) completely utilized lactic acid produced by the control organisms in the rumen fluid (Run 4). Of even more significance, regardless of the combination or organisms employed, *M. elsdenii* continued to show full utilization of lactic acid so that none could be detected. The preference exhibited by *M. elsdenii* for lactic acid is unexpected because numerous starch fermentation products such as glucose, fructose and maltose would be expected in the media. These sugars are known to be fermented by *M. elsdenii*.

Another aspect of the data from Table V is the shift in production of volatile fatty acids in favor of propionic acid and a reduction in the acetic/propionic acid (Ac/P) ratio. In Runs 15, 17, 19, 26, 28, 29, and 34, *M. elsdenii* was combined with organisms producing propionic acid. The Ac/P ratio was reduced while still accomplishing complete utilization of lactic acid.

EXAMPLE 3

Shift in VFA by *M. elsdenii* in Combination With Other Materials

Using the same procedures as in Example 2, *M. elsdenii* was combined with other organisms and with Rumensin (Ely Lilly brand of monensin). Results are set forth in Table VI.

lactic acid accumulation still occurred. With the addition of *M. elsdenii* (Runs 17-20), lactic acid was completely utilized while increases in propionic acid production were maintained.

ADMINISTRATION OF MICROORGANISMS TO THE ANIMAL

*M. elsdenii,* alone or in combination with propionic acid-producing microorganisms or substances are administered to the ruminant in a number of different ways. For example, cultures of *M. elsdenii,* alone or in combination, can be combined with an orally ingestible animal feed additive to form a supplement or premix to be added to standard feeds. The microorganisms can be added to the feed additive as broth or broth equivalent, paste or lyophilized cells. The microorganisms can also be encapsulated prior to addition to the feed additive. Dosage forms (e.g. drench of predetermined volume or capsules) can also be formed and, if desired, the microorganisms can be added directly to the animal feed, as by sprinkling the liquid broth over the feed. Where a premix is employed the feed manufacturer employs about one pound of premix per ton of finished feed. Typically, the premix should contain about $10^8$ to about $10^{14}$ microorganisms per pound. Where microorganisms in addition to *M. elsdenii* are used, the amounts set forth

TABLE VI

| Runs | Treatment[a] | pH | Molar % | | | | Ratio | $\mu$ Moles/ml | |
|---|---|---|---|---|---|---|---|---|---|
| | | | $Ac^f$ | $Pr^f$ | $Bu^f$ | $V_i$ | Ac/P | $L^c$ | $S^c$ |
| 1 | A | 4.9 | 79.3 | 15.2 | 5.5 | 0.0 | 5.2 | 53.5 | 0.0 |
| 2 | A | 4.9 | 78.8 | 15.5 | 5.7 | 0.0 | 5.1 | 49.8 | 0.0 |
| 3 | A & R | 4.9 | 78.5 | 17.1 | 4.4 | 0.0 | 4.6 | 56.8 | 0.0 |
| 4 | A & R | 4.9 | 78.7 | 17.1 | 4.2 | 0.0 | 4.6 | 56.0 | 0.0 |
| 5 | B | 5.15 | 63.0 | 30.6 | 6.4 | 0.0 | 2.1 | 40.5 | 0.0 |
| 6 | B | 5.2 | 62.4 | 31.1 | 6.5 | 0.0 | 2.0 | 33.5 | 0.0 |
| 7 | B & R | 5.0 | 63.2 | 31.5 | 5.3 | 0.0 | 2.0 | 53.2 | 0.0 |
| 8 | B & R | 5.0 | 62.2 | 32.2 | 5.6 | 0.0 | 1.9 | 56.4 | 0.0 |
| 9 | C | 5.4 | 46.8 | 20.2 | 27.5 | 5.5 | 2.3 | 0.0 | 0.0 |
| 10 | C | 5.4 | 46.9 | 20.3 | 27.2 | 5.6 | 2.3 | 0.0 | 0.0 |
| 11 | C & R | 5.35 | 37.5 | 24.0 | 30.2 | 8.3 | 1.6 | 0.0 | 16.4 |
| 12 | C & R | 5.35 | 38.3 | 23.5 | 30.1 | 8.1 | 1.6 | 0.0 | 10.6 |
| 13 | A,B,C | 5.15 | 59.4 | 18.7 | 18.5 | 3.4 | 3.2 | 0.0 | 0.0 |
| 14 | A,B,C | 5.2 | 58.8 | 19.5 | 18.3 | 3.4 | 3.0 | 0.0 | 6.2 |
| 15 | A,B,C + R | 5.15 | 57.4 | 21.2 | 18.0 | 3.4 | 2.7 | 0.0 | 7.8 |
| 16 | A,B,C, + R | 5.1 | 55.8 | 22.1 | 18.3 | 3.8 | 2.5 | 0.0 | 9.0 |
| 17 | B,C | 5.35 | 50.5 | 25.8 | 19.8 | 3.9 | 2.0 | 0.0 | 0.0 |
| 18 | B,C | 5.4 | 49.1 | 25.8 | 20.7 | 4.4 | 1.9 | 0.0 | 0.0 |
| 19 | B,C + R | 5.35 | 45.6 | 30.7 | 18.8 | 4.9 | 1.5 | 0.0 | 0.0 |
| 20 | B,C+R | 5.3 | 39.8 | 31.8 | 21.7 | 6.7 | 1.3 | 0.0 | 0.0 |
| 21 | A,B,C,D | 5.2 | 58.4 | 19.4 | 18.9 | 3.3 | 3.0 | 0.0 | 12.0 |
| 22 | A,B,C,D | 5.2 | 59.3 | 19.5 | 18.1 | 3.1 | 3.0 | 0.0 | 10.6 |
| 23 | A,B,C,D + R | 5.15 | 58.4 | 21.5 | 15.5 | 4.2 | 2.7 | 0.0 | 13.0 |
| 24 | A,B,C,D + R | 5.2 | 53.6 | 22.6 | 19.5 | 4.3 | 2.4 | 0.0 | 12.0 |
| 25 | Control | 5.15 | 69.1 | 23.6 | 7.3 | 0.0 | 2.9 | 59.0 | 0.0 |
| 26 | Control | 5.15 | 68.4 | 24.1 | 7.0 | 0.0 | 2.8 | 51.0 | 0.0 |
| 27 | R | 5.05 | 67.5 | 26.6 | 5.9 | 0.0 | 2.5 | 71.0 | 0.0 |
| 28 | R | 5.1 | 67.7 | 26.5 | 5.8 | 0.0 | 2.5 | 57.0 | 0.0 |

[a] A - *B. adolescentis*
B - *S. ruminantium*
C - *M. elsdenii*
D - *B. ruminicola*
R - Rumensin
[c] S - Succinic acid
L - Lactic acid
[f] The abbreviations Ac, Pr, Bu and V are as in preceeding Table V.

Rumensin is known to increase production of propionic acid and accomplished this result as shown in Runs 25-28. However, there was also a large accumulation of lactic acid. When *M. elsdenii* and Rumensin were combined (Runs 9-12), the Ac/P ratio was reduced while still utilizing all the lactic acid. In Runs 5-8, Rumensin was combined with *S. ruminantium,* an organism producing propionic acid. Large increases in propionic acid (as compared with control) were noted. However, herein below are employed. Suitable orally ingestible feed additives include distillers' dried grains, alfalfa, corn meal, citrus meal, fermentation residues, ground oyster shells, attapulgus clay, wheat shorts, molasses solubles, corn cob meal, edible vegetable substances, toasted dehulled soya flour, soybean mill feed, antibiotic mycelis, vermiculite, soya grits, crushed limestone and the like. The premix or supplement is added to standard feeds such as the so-called "concentrates" which are low in fiber and high in total digestible nutrients. This class includes the various grains and high grade by-products such as hominy feed, wheat bran, cottonseed meal, linseed meal, corn gluten feed, etc. The premix can also be added to roughage feeds, which are high in fiber, or mixtures of roughage and concentrate feeds.

DRENCH

The best and simplest way is simply to give the animal a drench of whole broth. Conveniently the broth can be prepackaged in cartridge form containing dosage ranges as described above or, the drench can be given by means of a conventional syringe. If the broth has gross material in it that might plug the orifice of the syringe, then it is preferred that the broth be given a coarse filtration prior to use. Prior to use the broth, whether or not filtered, can be stored. It will last three months without appreciable change if stored at a temperature of 0° to 4° C. Actually it can be stored at room temperature for about 1 week without harm. The reason for the latter possibility is that, when harvested at a pH of 6, there is still sufficient nutritional matter in the broth, so that if the microorganisms begin to grow again, for example by reason of failure of refrigeration, or by deliberate exposure to room temperature, the microorganisms will have available sufficient food for several days.

The amount of broth to be given an animal depends to some extent on the body weight of the animal. For example with steers, we have found that the volume of drench per 500–1,200 pounds of animal body weight should be in the range of about 3–20 ounces, suitably 12 ounces. This is given once a day, for as many days as the program requires. Generally, in converting a steer from roughage to concentrate, not more than three days is required to help the steer become adjusted.

A 12-ounce drench for steers is useful and typical. However, 3 and 6-ounce drenches can also be used. A drench volume in excess of 20 ounces is operable but is generally unnecessary. A 12-ounce drench contains $10^6$ to $10^{12}$ microorganisms as determined by the roll tube technique under anaerobic conditions. As is known, this method counts only viable organisms and of these, only organisms that will grow on this particular agar medium. The actual count is therefore presumed higher. Since $10^6$ to $10^{12}$ microorganisms is considered a typical dosage for a typical steer in the weight range of 500–1,200 lbs., these numbers may, if desired, be prorated to obtain dosages for other ruminants, i.e., cattle, sheep, and goats, weighing more or less than the said 500–1,200 lb. weight range, and whether the animal is well or sick. Actually, as a practical matter a 12-ounce drench of whole broth is believed to be usable for all ruminants regardless of species or weight. It has been found that the range for *S. ruminantium* in whole broth is from about $10^8$ to about $10^9$ microorganisms/ml. In treating ruminants, a ratio (*elsdenii/ruminantium*) of 1 to 1 is employed. Based on the Examples, it has been found that at least 20% of the microorganisms in whole broth should be *M. elsdenii* with the remainder being other organisms, such as those producing propionic acid.

PASTE IN CAPSULES

Additionally, whole broth usable in drenches can be converted to a microbial cell paste which is obtained by centrifugation or filtration of the broth with a carrier, as for example, a mixture of sugar (e.g. lactose) and cellulose. A unit dosage form is obtained by transfer of the paste to a gelatin or other type conventional capsule known in the art. The capsules can be stored at normal refrigeration temperatures if they are to be used within a short period of time. For long term storage, it is preferable to store the capsules in a frozen state. The capsules can be administered via bolus gun. Each capsule should contain from about $10^6$ to about $10^{12}$ microorganisms. Capsule unit dosage forms can also be formed from lyophilized cells in which each capsule contains from about $10^6$ to $10^{12}$ microorganisms per capsule. In addition to the carrier, the microorganisms can be blended or mixed with orally ingestible diluents, fillers, binders, lubricants and like excipients by conventional formulation techniques.

DIRECT ADDITION TO FEED

In another method of administration, the bacteria can be added directly to the animal feed, e.g., by pouring broth on the feed, or by adding encapsulated microorganisms to the feed, or by mixing centrifuged (or filtered) paste with the feed. Other modes of addition are also suitable. In this method, the microorganisms can be microencapsulated using techniques to minimize processing exposure to oxygen and coating materials which are minimally permeable to oxygen and other materials in the dry feed which are noxious to the microorganisms, but which coating materials readily dissolve in the rumen fluids when ingested by the ruminant thereby releasing the live and unaltered microorganisms. Methods of microencapsulation are disclosed, e.g., in U.S. Pat. Nos. 2,800,457 and 2,800,458. Such microencapsulated microorganisms are preferably admixed with the specific feedstuffs to be fed the ruminants.

The amount of *M. elsdenii*, however added, should be sufficient to provide about $10^6$ to $10^{12}$ microorganisms per day. For a ruminant eating 30–50 lbs. of total feed/day (concentrate and forage), this means the addition of about $10^8$ to $10^{14}$ microorganisms/lb. of feed. Broth made by the preceding examples (and starting from the ARM material) normally contains $10^8$ to $10^{10}$ microorganisms/ml, or about $10^9$ to $10^{11}$/ounce, or about $10^{10}$ to $10^{12}$ per 12 ounces, but the count may vary somewhat from batch to batch. Bacteria counts are readily made by those skilled in the art, so this feature is easily determined. Accordingly, then, in a typical and simple case, 12 ounces of broth (screened or unscreened) can be added directly to the feed to provide about $10^{10}$ to $10^{12}$ microorganisms.

FREEZING

Another method of preparing *M. elsdenii* and other microorganisms for administration to the ruminant is to freeze the broth as soon as it is ready for use. This is done by any of several means including placing the container of microorganisms into an acetone dry ice bath, placing said container in liquid nitrogen, or placing said container into a freezer. Generally, it is desirable to lower the temperature of the additive to about −20° C. The amount of time required to attain this temperature varies with the method used and takes only a matter of seconds when liquid nitrogen is used, to an hour when a freezer is utilized. At a later time the additive can be thawed and spread over the feed.

LYOPHILIZATION

Another method of preparing the microorganisms for administration is to freeze-dry the whole broth, (i.e., the cultured aqueous suspension prepared as in Example 1). This is accomplished by centrifuging the whole broth until approximately 9/10 of it can be decanted; decanting and adding 10% based upon the weight of the remaining whole broth of glucose to the remaining whole broth; freezing this mixture in a refrigerator; placing the frozen mixture into a drier; subjecting it to reduced pressure, and allowing the frozen mixture to gradually warm to room temperature. When needed, the additive can be mixed with an inert carrier and applied across the feed.

When the additive is frozen or freeze-dried, it is preferable to mix the whole broth with a cryo-protective agent such as glycerol, sucrose, glucose, casein, and whey. A suitable ratio is 100 parts of whole broth or broth equivalent to 6 parts of cryo-protective agent. The purpose of the cryo-protective agent is, of course, to protect the microorganisms from damage during the freezing process. If monensin is employed, the normal procedures, e.g. dosage level and method of administration are utilized. For example, monensin can be admixed with the feed using from 2.5 to 25 mg/lb of feed.

EXAMPLE 4

In Vivo Study

To confirm the in vitro studies described above, a 1-liter drench of *M. elsdenii* was administered to cattle immediately prior to beginning a 30-day adaptation cycle to high concentrate feed. The control group received equivalent amounts of uninoculated broth medium, i.e. the inoculum did not contain the test bacteria. Prior to the 30-day period, the animals had been fed a high roughage diet. The results as set forth in Table VII illustrate that *M. elsdenii* produced increased weight gain and feed efficiency as compared with the control group. The combination of *M. elsdenii* with *S. ruminantium* exhibited outstanding results.

TABLE VII

| No. of Animals | Treatment* | Init. Wt. | Final Wt. | Daily Gain | Daily Feed | Efficiency |
|---|---|---|---|---|---|---|
| 5 | Control | 733.2 | 775.8 | 1.42 | 15.64 | 11.01 |
| 5 | " | 732.8 | 770.6 | 1.26 | 15.75 | 12.50 |
| 5 | " | 742.8 | 790.2 | 1.58 | 15.80 | 10.00 |
| 5 | " | 718.4 | 789.4 | 2.37 | 15.72 | 6.63 |
|   |   |   |   | $1.66^a$ |   | $10.04^a$ |
| 5 | *M. elsdenii** | 781.2 | 832.6 | 1.71 | 15.93 | 9.32 |
| 5 | " | 702.4 | 751.2 | 1.63 | 15.72 | 9.64 |
| 5 | " | 703.0 | 766.0 | 2.10 | 15.37 | 7.32 |
| 5 | " | 741.6 | 787.0 | 1.51 | 16.30 | 10.79 |
|   |   |   |   | $1.74^a(+4.8\%)$** |   | $9.27^{ab}(+7.7\%)$ |
| 5 | *M. elsdenii** & *S. ruminantium* | 688.4 | 742.0 | 1.79 | 15.50 | 8.66 |
| 5 | " | 749.2 | 817.0 | 2.26 | 16.29 | 7.21 |
| 4*** | " | 701.0 | 775.5 | 2.48 | 16.16 | 6.52 |
| 5 | " | 732.0 | 786.4 | 1.81 | 15.70 | 8.67 |
|   |   |   |   | $2.09^a(+25.9\%)$ |   | $7.77^{ab}(+22.6\%)$ |

*Each animal received one liter of the respective treatment before receiving the 85% concentrate ration.
**Positive response over the Control animals.
***One animal died of pneumonia on October 12, 1976 as verified by post-mortem examination.
$a,ab$ Values sharing the same superscript are not statistically different (p < .05).

Culture preparation for the in vivo study was essentially as described above except that the PYG broth described in Table III was replaced with a lactate medium having the composition set forth in Table VIII.

TABLE VIII

| Yeast extract | 0.4 | gm |
|---|---|---|
| Peptone | 0.5 | gm |
| Lactic acid (85%) | 0.753 | ml |
| $KH_2PO_4$ | 0.05 | gm |
| $MgCl_2 \cdot 6H_2O$ | 0.03 | gm |
| $NH_4Cl$ | 0.05 | gm |
| Resazurin | 0.4 | ml |
| Cystein HCl $\cdot H_2O$ | 0.05 | gm |
| Distilled $H_2O$ | 100 | ml |

What is claimed is:

1. A composition for facilitating the adaptation of ruminants from a roughage or normal pasture ration to a high energy ration, comprising a mixture of bacterial cultures consisting essentially of Megasphaera elsdenii and Selenomonas ruminantium, said cultures admixed with an orally ingestible animal feed additive, selected from the group consisting of dried grains, alfalfa, corn meal, citrus meal, fermentation residues, ground oyster shells, attapulgus clay, wheat shorts, molasses solubles, corn cob meal, edible vegetable substances, toasted dehulled soya flour, soybean mill feed, antibiotic mycelis, vermiculite, soya grits and crushed limestone, said composition reducing or eliminating the symptoms of lactic acidosis during adaptation of said ruminants to said high energy ration.

2. A composition as in Claim 1 wherein the bacterial cultures are employed in the form of a dehydrated concentrate.

3. A composition as in claim 1 wherein monensin is employed to facilitate production of propionic acid.

4. A composition in unit dosage form for facilitating the adaptation of ruminants from a roughage or normal pasture ration to a high energy ration, comprising (a) a mixture of bacterial cultures consisting essentially of *Megasphaera elsdenii* and *Selenomonas ruminantium* and (b) a carrier, said dosage form containing $10^6$ to $10^{12}$ microorganisms per dose.

5. A composition as in claim 4 in the form of a capsule.

6. A composition as in claim 4 wherein the bacterial cultures are in the form of a dehydrated concentrate.

7. A composition as in claim 4 wherein the cultures are dispersed in an aqueous carrier.

8. A method of facilitating the adaptation of ruminants from a roughage or normal pasture ration to a high energy ration comprising administering to said ruminant an amount of a bacterial culture consisting essentially of Megasphaera elsdenii and Selenomonas ruminantium effective to reduce symptoms of lactic acidosis during said adaptation.

9. A method as in claim 8 wherein the culture is in the form of a dehydrated concentrate.

10. A method as in claim 8 wherein the culture is dispersed in an aqueous carrier.

11. A method as in claim 8 further comprising the step of administering monensin to enhance ruminal production of propionic acid in said animal.

12. A method as in claim 8 wherein the bacterial culture is combined with a carrier, said combination being employed in unit dosage form containing $10^6$ to $10^{12}$ *microorganisms per dose.*

13. A composition for facilitating the adaptation of ruminants from roughage or normal pasture rations to a high energy starch ration, consisting essentially of a bacterial culture of Megasphaera elsdenii and a propionic acid producing bacterial culture, said composition in unit dosage form containing $10^6$ to $10^{12}$ microorganisms.

14. A composition as in claim 13 wherein the propionic acid-producing culture is Selenomonas ruminantium.

* * * * *